United States Patent [19]

Stepto et al.

[11] Patent Number: 4,767,846

[45] Date of Patent: Aug. 30, 1988

[54] PRODUCTION OF POLYMERIC POLYOLS

[75] Inventors: Robert F. T. Stepto, Poynton; Richard H. Still, Disley, both of England; Yoji Hirasawa, Yawata, Japan

[73] Assignees: Nippon Paint Company Limited, Osaka, Japan; The University of Manchester Institute of Science and Technology, Manchester, England

[21] Appl. No.: 941,783

[22] Filed: Dec. 2, 1985

Related U.S. Application Data

[63] Continuation of Ser. No. 619,403, Jun. 12, 1984, abandoned, which is a continuation of Ser. No. 393,943, Jun. 30, 1982, abandoned.

[30] Foreign Application Priority Data

Jul. 4, 1981 [GB] United Kingdom ................ 8120726

[51] Int. Cl.$^4$ .............................................. C07H 1/00
[52] U.S. Cl. .................... 536/18.6; 536/18.3; 536/120; 568/620
[58] Field of Search ...................... 536/120, 126, 18.6, 536/18.3; 368/620

[56] References Cited

U.S. PATENT DOCUMENTS

| | | | |
|---|---|---|---|
| 3,317,508 | 5/1967 | Winquist et al. | 536/120 |
| 3,370,056 | 2/1968 | Yotsuzuka et al. | 568/620 |
| 3,442,888 | 5/1969 | Degginger et al. | 536/120 |
| 3,445,525 | 5/1969 | Bonmann et al. | 568/620 |

FOREIGN PATENT DOCUMENTS

| | | | |
|---|---|---|---|
| 722733 | 11/1965 | Canada | 568/620 |
| 778239 | 7/1957 | United Kingdom | 568/620 |

*Primary Examiner*—J. R. Brown
*Assistant Examiner*—Elli Peselev
*Attorney, Agent, or Firm*—Sughrue, Mion, Zinn, Macpeak & Seas

[57] ABSTRACT

Polymeric polyols are prepared by reacting a polyhydroxy initiator compound with an epoxide in the presence of alkali metal hydroxide catalyst used in an amount of at least 10% by mole based on the molar amount of polyhydroxy initiator compounds. The polyols so obtained may be chain extended by reaction with further epoxide in the presence of at least 10% by mole of an alkali metal hydroxide catalyst based on the molar amount of the polymeric polyol.

12 Claims, No Drawings

PRODUCTION OF POLYMERIC POLYOLS

This is a continuation application of Ser. No. 619,403, filed on June 12, 1984, now abandoned, which is a continuation of application Ser. No. 393,943, filed June 30, 1982, now abandoned.

The present invention relates to the manufacture of polymeric polyols.

Polymeric polyols are products which may be obtained by the generally catalysed reaction between a polyol initiator compound (e.g. pentaerythritol) and an epoxide compound, i.e. one containing a three member ring of two carbon atoms and one oxygen atom, (e.g. propylene oxide). The reaction generally proceeds by proton removal from the polyol followed by nucleophilic attack on the epoxide ring forming an ether linkage between the polyol and epoxide compound residues and a new nucleophilic grouping (derived from the epoxide oxygen) on the epoxide compound residue. Each hyroxyl group of the polyol may react with an epoxide molecule, and then chain extension may take place by reaction of the generated nucleophilic grouping on the epoxide residue with further free epoxide compound.

The term polymeric polyols is generally applied to cover products in which one or more cyclic oxide residues are added to the initiator compound, although when only one or two such groups are added the products are perhaps more correctly described as adducts. For simplicity however the term "polymeric polyols" is used herein to cover any product obtained by reaction of an initiator with one or more molecules of an epoxide.

Polymeric polyols may be reacted with di- or higher functionality isocyanate compounds to produce polyurethanes. The properties of the polyurethanes depend, at least to a certain extent, on the nature of the polymeric polyol starting material. A polymeric polyol having a functionality of at least 3 ensures that a cross-linked polyurethane network is produced. Polymeric polyols of lower functionality, e.g. caused by unsaturation at the chain ends, can produce polyurethanes which may have unsatisfactory properties because of the resulting deficient network structure. It is also preferred that the polymeric polyols have a high molecular weight since we have established that the hydroxyl groups of low molecular weight polyols show unequal reactivity towards isocyanate groups due, for example, to steric hindrance. This also leads to deficiencies in the network structure as unreacted hydroxyl groups react with free isocyanate groups on the same growing polyurethane molecule to form rings.

Polymeric polyols may also be used for producing polyesters and the same considerations apply as those discussed above.

Prior syntheses for producing polymeric polyols have a number of disadvantages, particularly when the polyol initiator has a funtionality of 4 or more. These difficulties arise partly from the fact that such high functionality polyols are generally high melting solids (pentaerythritol m.pt.ca 260° C.) and the reaction conditions required by prior syntheses are not conducive to efficient polymeric polyol formation.

For example, U.K. Pat. No. 891,776 describes a process in which a solution or dispersion generally aqueous, of high functionality polyol initiator (e.g. pentaerythritol, sorbitol) reacts with the epoxide (e.g. propylene oxide) in the presence of a catalyst (e.g. potassium hydroxide). The amount of catalyst employed is significantly less than 1% by mole per mole of polyol starting material. In this and other processes employing solvents by-products are formed by reaction of solvent with epoxide. The process of U.K. Pat. No. 891,776 is conducted up to a point at which the product formed between the epoxide and polyol initiator is a liquid and the by-products and solvent are removable by distillation. At this point the polymeric polyol has a comparatively low molecular weight, e.g. that formed between pentaerythritol and propylene oxide has a number average molecular weight of ca 220–235. After removal of the by-products and solvent by distillation, further reaction of the liquid polymeric polyol with epoxide is required to increase the molecular weight. We have found that reaction of the aforementioned pentaerythritol/propylene oxide of molecular weight ca 220–235 yields a polymeric polyol of molecular weight ca 410 in one further stage.

Obviously the more stages required to obtain a particular molecular weight the higher the cost of the final product.

It is an object of the invention to obviate or mitigate the above disadvantages.

According to the present invention there is provided a method of producing a polymeric polyol comprising reacting a polyhydroxy compound (as herein defined) with an epoxide (as herein defined) in the presence of an alkali metal hydroxide catalyst used in an amount of at least 10% by mole based on the molar amount of polyhydroxy compound.

The term polyhydroxy compound as used herein refers to compounds containing 3 or more hydroxyl groups. The term epoxide compound refers to compounds which include a three membered ring of two carbon atoms and one oxygen atom.

The method of the invention allows the one stage synthesis from polyhydroxy compound of polymeric polyols having molecular weights which were previously only attainable by a two stage synthesis (e.g. in accordance with U.K. Pat. No. 891,776). The product of the one stage synthesis may be chain extended by reaction with further epoxide compound, as described more fully below, to produce polymeric polyols having molecular weights much in excess of those previously attainable. Particularly in the one stage process, there is a low incidence of by-product formation and the polymeric polyols formed are of low unsaturation and high functionality. These effects are surprising having regard to the high concentration of catalyst used (greater than 10% by mole per mole of polyhydroxy compound). At such high catalyst levels it would be expected that the alkali metal hydroxide would promote unwanted reactions between epoxide molecules, causing oligomer formation, as well as unwanted reactions between epoxide and solvent or dispersing-medium (when used). Additionally, loss of functionality of the polymeric polyols could be expected to occur at such high catalyst concentrations.

We have not conducted mechanistic studies to explain the unexpected course of the reaction of the invention but we believe that the catalyst preferentially reacts with the polyol thus substantially precluding attack of the catalyst on the epoxide molecule and avoiding by-product formation. The nucleophile derived from the polyol may then effect an attack on the epoxide ring in known manner.

The invention is applicable particularly to the production of polymeric polyols from polyhydroxy compounds having 4 or more hydroxy groups. Such polyhydroxy compounds are as mentioned above generally high melting solids which it has been difficult to convert efficiently to polymeric polyols by prior synthesis. Examples of such polyhydroxy compounds for use in the invention are triols, tetrols, pentols, hexols and higher functionality polyols. The polyols may, for example, be monosaccharide, disaccharide or trisaccharide sugars. The invention is particularly applicable when the polyhydroxy compound is pentaerythritol (a tetrol), D-sorbitol (a hexol) or sucrose (a disaccharide).

A number of epoxides may be used. Most suitable however are alkylene oxides, such as ethylene oxide or propylene oxide. Propylene oxide is most convenient because it is a liquid and easy to handle at room temperature. Mixtures of epoxides may also be employed.

The catalyst concentration will for preference be 10-20% by mole per mole of polyhydroxy compound, although the use of higher catalyst concentrations is not precluded. Potassium hydroxide is particularly preferred as the catalyst.

Most preferably the reaction is conducted in a solvent or dispersing medium, for example water.

The synthesis of the invention is for preference conducted at raised temperature to provide shorter reaction times. However, we have found that temperatures above 100° C. significantly increase the unsaturation content, thereby reducing functionality. A reaction temperature of ca 90°-95° C. is, we believe optimum in allowing reasonable reaction times without high unsaturation. For certain applications however a high unsaturation may be tolerable in which case reaction temperatures above 100° C. may be employed. Reactions are preferably conducted in an autoclave at the required temperature and at a suitable pressure, e.g. up to 200 psi more preferably up to 30 psi (both pressures being absolute values). One convenient procedure is to raise the temperature of the autoclave (containing the reactants) to a suitable temperature and then allow the autoclave to cool. Alternatively the autoclave may be maintained at the reaction temperature for any desired time.

Polymeric polyols obtained by reaction of the polyhydroxy compound initiator and epoxide compound are generally oils. These products may, as mentioned above be reacted with further epoxide compound (either the same or a different epoxide from that employed in the first stage) to increase molecular weight significantly by chain extension. This chain extension reaction may be conducted in the presence of a solvent (which may be the epoxide compound if liquid) using an alkali metal hydroxide catalyst. However the presence of water is undesirable for the chain extension reaction, and when water is present in the product to be chain extended it should initially be eliminated, e.g. by distillation. The amount of catalyst employed in the chain extension stage should be at least 10% by mole per mole of polymeric polyol. Most preferably, the amount of catalyst is 10-80% on the same basic. Best results are obtained when the catalyst is finely-divided, preferably with a particle size below 0.3 mm, more preferably below 0.1 mm.

Polymeric polyols obtained by the method of the invention (either by a one-stage process or by chain extension of products from such a process) have a high retention of functionality based on the functionality of the polyhydroxy initiator compound. In other words the polymeric polyol has a functionality approaching that of the polyhydroxy initiator compound. This can be demonstrated by gelation studies. This high, functionality of the products, together with the range of molecular weights in which they may be produced, renders the products suitable for producing a range of polyurethanes which will have a high junction-point density.

It is envisaged that the polymeric polyols will find particular application in formulations for use in Reaction Injection Moulding (RIM) and Reinforced Reaction Injection Moulding (RRIM) processes in which a polyurethane is formed and fabricated in situ in a mould by injection therein of polymeric polyol or polyols, isocyanate reactants and suitable additives (e.g. catalysts and fillers). In such RIM and PRIM processes a polyol produced by the method of the invention may be used alone, in combination with other polyols so produced or with other suitable polyols.

Polyurethanes prepared from the polymeric polyols will also be useful for paints and coatings.

The invention is illustrated by reference to the following non-limiting Examples. For convenience the Examples are divided into two Sections. Section 1 illustrates the one stage production of polymeric polyols by the method of the invention as well as providing a comparison of this method with a similar prior art synthesis. Section 2 illustrates the chain extension of polymeric polyols produced in Section 1.

SECTION 1

The following general method was used for each of Examples 1.1-1.4 and Comparative Examples C1-C4, details of specific reactants amounts being given under the particular Examples. A suspension/solution was prepared from the indicated polyol, propylene oxide potassium hydroxide, and water. The amount of catalyst was approximately 20% by mole per mole of polyol starting material, and the amount of water was approximately half the weight of polyol.

The suspension was introduced into an autoclave which was then sealed and pressurised to 30 psi with nitrogen gas. The autoclave was then heated to 95° C. over a period of 30 minutes and subsequently allowed to cool to room temperature, except where the temperature was held at 95° C. for the stated times before the autoclave was allowed to cool. The reaction mixture was stirred throughout heating and cooling.

The reaction products were firstly purified in a rotary film evaporator for five hours at a temperature of 100° C. under a pressure of 5 mm Hg. Unwanted reactant polyol and catalyst were then removed by dissolution of the product in propylene oxide followed by filtration. Excess propylene oxide was then removed by a rotary film evaporator.

In the Examples, molecular weights are number average molecular weights.

EXAMPLE 1.1

| | |
|---|---|
| Pentaerythritol | 340 g (2.5 mole) |
| Propylene oxide | 320 ml |
| Potassium hydroxide | 28 g (0.5 mole) |
| Water | 170 ml |
| Product: Oxypropylated pentaerythritol (I) | |
| Molecular weight | 420 g mol$^{-1}$ (by chemical determination of hydroxyl groups) |
| Unsaturation | 0.17 mol % C=C (mol OH)$^{-1}$ |

-continued (by Wij's method)

G.P.C. analysis and gelation studies indicate the absence of linear polymeric oxides

EXAMPLE 1.2

| Pentaerythritol | 340 g (2.5 mole) |
|---|---|
| Propylene oxide | 320 ml |
| Potassium hydroxide | 28 g (0.5 mole) |
| Water | 170 ml |
| Product: Oxypropylated pentaerythritol (II) | |
| Molecular weight | 516 g mol$^{-1}$ (by chemical determination of hydroxyl groups) |
| Unsaturation | 0.01 mol % C=C (mol OH)$^{-1}$ (by Wij's method) |

The differences in the products of examples 1.1 and 1.2 are caused by slight variations in the described purification procedure (amount of propylene oxide and time of contact of the propylene oxide with the autoclave products).

In Example 1.1 the volume of propylene oxide used for purification was approximately the same as that of the product mixture obtained from the first treatment in the rotary film evaporator and the contact time was about 1 hour. In the purification procedure of Example 1.2 a 30% by volume excess of propylene oxide and a contact time of about 12 hours were employed.

EXAMPLE 1.3

| Sorbitol | 182 g (1 mole) |
|---|---|
| Propylene oxide | 264 ml |
| Potassium hydroxide | 11.2 g (0.2 mole) |
| Water | 78 ml |
| Product: Oxypropylated sorbitol (I) | |
| Molecular weight | 439 g mol$^{-1}$ (by chemical determination of hydroxyl groups) |
| Unsaturation | 0.01 mol % C=C (mol OH)$^{-1}$ (by Wij's method) |

EXAMPLE 1.4

| Sucrose | 266 g (0.777 mole) |
|---|---|
| Propylene oxide | 176 ml |
| Potassium hydroxide | 8.7 g (0.155 mole) |
| Water | 67 ml |
| Reaction Time at 95° C. | 2 hrs. |
| Product: Oxypropylated suorose (I) | |
| Molecular weight | 529 g mol$^{-1}$ (by chemical determination of hydroxyl groups) |
| Unsaturation | 0.01 mol % C=C (mol OH)$^{-1}$ (by Wij's method) |

COMPARATIVE EXAMPLE C1

| Pentaerythritol | 340 g (2.5 moles) |
|---|---|
| Propylene oxide | 320 ml |
| Potassium hydroxide | 3 g (0.05 moles) |
| Water 170 | 170 ml |

As will be appreciated from the above, the amount of catalyst (potassium hydroxide) is 2% by mole per mole of polyol starting material, as compared with 20% as used in the Examples.

| Product: Oxypropylated Pentaerythritol | |
|---|---|
| Molecular weight | 265 g mol$^{-1}$ (by chemical determination of hydroxyl groups) |
| Unsaturation | 0.087 mol % C=C (mol OH)$^{-1}$ (by Wij's method) |

A comparison between Example 1.1 and Comparative Example C1 clearly demonstrates that the use of higher catalyst amounts (20% by mole) gives products of significantly higher molecular than when lower catalyst amounts are used.

COMPARATIVE EXAMPLE C2-C4

Comparative Example C1 was repeated save that the autoclave was held at 95° C. for varying times to see whether increased reaction time would increase the molecular weight of the product. The results are shown in Table I.

TABLE I

| Comparative Example | Reaction Time at 95° C./hr | M. Wt./ g mol$^-$ | Unsaturation/ mol % C=C/mol OH |
|---|---|---|---|
| C2 | 1.0 | 265 | 0.14 |
| C3 | 1.5 | 264 | 0.11 |
| C4 | 3.0 | 266 | 0.13 |

Increasing the reaction time thus provided no increase in Molecular Weight, once again demonstrating the advantage of using higher catalyst amounts.

SECTION 2

The products of Examples 1.1-1.4 were subjected to chain extension by propylene oxide. Reaction was effected in a first stage by dissolving the appropriate product from Examples 1.1-1.4, and from which water and low molecular weight volatiles had been removed, in at least its own weight of propylene oxide and using an amount of catalyst (potassium hydroxide) of at least 20% by mole per mole of the polymeric polyol reactant. The products from this first stage could be reacted in at least one subsequent second stage with further propylene oxide to provide further molecular weight increase. The first and subsequent stage of the chain-extension reaction could be conducted at room temperature under atmospheric pressure, or more suitably in an autoclave at increased temperature and pressure. Products were purified as described under Section 1. Specific reaction details are given under each Example.

Chain Extension of Oxypropylated Pentaerythritol Polymers

EXAMPLE 2.1

| Oxypropylated pentaerythritol (I) | 100 g (0.24 mole) |
|---|---|
| Propylene oxide | 200 ml |
| Potassium hydroxide | 2.7 g (0.048 mole) |
| Molar Ratio Catalyst: Oxypropylated pentaerythritol (I) | 20% |
| Reaction details: room temperature, atmospheric pressure, 4 days | |
| Product: Oxypropylated pentaerythritol (III) | |
| Molecular weight | 567 g mol$^{-1}$ (by chemical determination of hydroxyl groups) |

| | |
|---|---|
| Unsaturation | 0.13 mol % C=C (mol OH)$^{-1}$ (by Wij's method) |

Example 2.3, were obtained by a cone and plate viscometer. The significance of the viscosity results is discussed below.

TABLE II

| Example No. | Cat. content Mol %/mol polyol | Reaction temp. °C. | Reaction time | Molecular weight | mol % C=C/mol OH | Viscosity cp |
|---|---|---|---|---|---|---|
| 1.2 | — | — | — | 516 | — | 1224 |
| 2.4 | 80 | 95 | 0 hrs | 922 | 0.11 | 380 |
| 2.5 | " | 95 | 1.0 hrs | 1259 | 0.33 | 307 |
| 2.3 | " | 90–95 | 2.5 hrs | 3560 | 5.27 | 401 |
| 2.6 | " | 85–90 | 7.0 hrs | 5600 | 12.76 | 574 |

G.P.C analysis and results of gelation studies indicate the absence of linear polymeric oxides.

EXAMPLE 2.2

| | |
|---|---|
| Oxypropylated pentaerythritol (III) | 112 g (0.198 mole) |
| Propylene oxide | 587 ml |
| Potassium hydroxide | 4.4 g (0.079 mole) |
| Molar Ratio Catalyst: Oxypropylated Pentaerythritol (II) | 40% |

Reaction details: Autoclave heated to 95° C. over 0.5 hours, held at 95° C. for 3 hours, and then allowed to cool. Pressure 30 psi.

Product: Oxypropylated pentaerythritol

| | |
|---|---|
| Molecular weight | 1920 g mol$^{-1}$ (by chemical determination of hydroxyl groups) |
| Unsaturation | 1.20 mol % C=C (mol OH)$^{-1}$ (by Wij's method) |

G.P.C. analysis and results of gelation studies indicate the absence of linear polymeric oxides.

EXAMPLE 2.3

| | |
|---|---|
| Oxyproylated pentaerythritol (II) | 59 g (0.114 mole) |
| Propylene oxide | 645 ml |
| Potassium hydroxide | 5.0 g (0.089 mole) |
| Molar Ratio Catalyst: Oxypropylated Pentaerythritol (II) | 80% |

Reaction details: As for Example 2.2 except that the temperature of the autoclave was maintained for 2.5 hrs.

Product: Oxypropylated pentaerythritol

| | |
|---|---|
| Molecular weight | 3560 g mol$^{-1}$ (by chemical determination of hydroxyl groups) |
| Unsaturation | 5.27 mol % C=C (mol OH)$^{-1}$ by Wij's method) |

EXAMPLES 2.4–2.6

Oxypropylated pentaerythritol II was reacted with propylene oxide and potassium hydroxide in an autoclave in a series of reactions conducted under essentially the same conditions but for different reaction times and then purified as previously to investigate the effect of reaction time on molecular weight. The conditions employed as well as the results obtained are shown in Table II below. By way of explanation, the reactants were heated in the autoclave over a period of ca 0.5 hour to reach the reaction temperature. The reaction time is the time for which the autoclave is held at the reaction temperature before cooling.

The viscosities in Table II, which includes that of the product of Example 1.2 for comparison and that of

Chain Extension of Oxypropylated Sorbitol Polymers

EXAMPLE 2.7

| | |
|---|---|
| Oxypropylated sorbitol (I) | 300 g (0.68 mole) |
| Propylene oxide | 450 ml |
| Potassium hyroxide | 8.4 g (0.15 mole) |
| Molar Ratio Catalyst: Oxypropylated sorbitol (I) | 22% |

Reaction details: room temperature, atmospheric pressure, 5 days

Product: Oxypropylated sorbitol (II)

| | |
|---|---|
| Molecular weight | 901 g mol$^{-1}$ (by chemical determination of hydroxyl groups) |
| Unsaturation | 0.06 mol % C=C (mol OH)$^{-1}$ (by Wij's method) |

EXAMPLE 2.8

| | |
|---|---|
| Oxypropylated sorbitol (II) | 100 g (.11 mole) |
| Propylene oxide | 300 ml |
| Potassium hydroxide | 1.4 g (0.025 mole) |
| Molar Ratio Catalyst: Oxypropylated Sorbitol (II) | 22% |

Reaction details Autoclave 80° C., 30 psi, 14 hrs.

Product: Oxypropylated sorbitol

| | |
|---|---|
| Molecular weight | 2462 g mol$^{-1}$ (by chemical determination of hyrdoxyl groups) |
| Unsaturation | 0.53 mol % C=C (mol OH)$^{-1}$ (by Wij's method) |

The viscosities of the products of Examples 1.3, 2.7 and 2.8 were measured using a cone and plate viscometer and the results, discussed more fully below, are shown in Table III.

TABLE III

| Product of Example No. | M. Wt. | Viscosity cp |
|---|---|---|
| 1.3 | 439 | 7018 |
| 2.7 | 901 | 1720 |
| 2.8 | 2462 | 377 |

Chain Extension of Oxypropylated Sucrose Polymers

EXAMPLE 2.9

| | |
|---|---|
| Oxypropylated sucrose (I) | 300 g (0.57 mole) |
| Propylene oxide | 300 ml |
| Potassium hydroxide | 6.0 g (.11 mole) |
| Molar Ratio Catalyst: Oxypropylated sucrose (I) | 20% |

Reaction details: room temperature, atmospheric pressure 40 days.

Product: Oxypropylated sucrose (II)

-continued

| Molecular weight | 1326 g mol$^{-1}$ (by chemical determination of hydroxyl groups) |
| --- | --- |
| Unsaturation | 0.05 mol % C=C (mol OH)$^{-1}$ (by Wij's method) |

EXAMPLE 2.10

| Oxypropylated sucrose (II) | 200 g (0.15 mole) |
| --- | --- |
| Propylene oxide | 300 ml |
| Potassium hydroxide | 4.8 g (0.085 mole) |
| Molar Ratio Catalyst: Oxypropylated Sucrose (II) | 56% |

Reaction details: Autoclave 85° C., 30 psi, 2 hrs.
Product: Oxypropylated sucrose

| Molecular weight | 2228 g mol$^{-1}$ (by chemical determination of hydroxyl groups) |
| --- | --- |
| Unsaturation | 0.12 mol % C=C (mol OH)$^{-1}$ (by Wij's method) |

The viscosities of the products of Examples 2.9 and 2.10 were determined by a cone and plate viscometer and are shown in Table IV below.

TABLE IV

| Product of Example No. | Molecular Weight | Viscosity cp |
| --- | --- | --- |
| 2.9 | 1326 | 10834 |
| 2.10 | 2228 | 727 |

A consideration of the results of the Examples clearly illustrates the significant advance of the invention. As shown in Section 1 the inventive method yields in one stage, polymeric polyols having molecular weights substantially higher than those obtained by conventional one-stage synthesis using lower catalyst amounts. In fact, the methods described in Section 1 achieve molecular weights which would generally require a two stage synthesis by conventional methods.

The products obtained from Section 1 may be used to produce a range of higher molecular weight polyols either by
 (a) a series of reaction stages, as exemplified by the pairs of Examples 2.1 and 2.2, or 2.7 and 2.8 or 2.9 and 2.10; or
 (b) by increasing the second stage reaction time at a given temperature as exemplified by Examples 2.3-2.6

The polymeric polyols produced generally have low unsaturation thus indicating a high retention of functionality, i.e. a polymeric polyol from pentaerythritol will have a functionality approaching 4. This can be demonstrated be gelation studies on the polymeric polyol.

An interesting feature of the products is illustrated by the viscosity results in Tables (II)-(IV). Table (II) shows that viscosity of oxypropylated pentaerythritol polymers decreases as molecular weight increases to a value, above which viscosity increases. Tables (III) and (IV) show a similar decrease in viscosity with increasing molecular weight for products based on sorbitol and sucrose. It is anticipated that increasing the molecular weight of these sucrose and sorbitol polymers will lead to a viscosity minimum as for the pentaerythritol based products. As far as we are aware this effect has not been observed in polymeric polyols produced by conventional methods.

The invention thus achieves a range of polymeric polyols of high functionality which are eminently suitable for producing a range of polyurethanes by known methods. The viscosity behaviour discussed above is significant because high molecular weight polymeric polyols required for certain polyurethanes may, because of their low viscosity, be handled easily whilst still providing the benefits of their high molecular weight in the finished polyurethane.

What is claimed is:

1. In a process of producing a polymeric polyol in an aqueous reaction system in the presence of an alkali metal hydroxide catalyst, the improvements to produce a polymeric polyol of high molecular weight, low unsaturation and high functionality with reduced by-product in a single stage of reaction which comprises reacting in a single stage of reaction only one kind of a polyhydroxy compound having at least three hydroxyl groups in its molecule and being selected from the group consisting of tetrols, pentols, hexols, and monosaccharide, disaccharide and trisaccharide sugars with ethylene oxide, propylene oxide or a mixture thereof in the presence of an alkali metal hydroxide catalyst used in an amount of 10% to 20% by mole based on the molar amount of polyhydroxy compound, said reaction being carried out in the presence of a liquid medium essentially consisting of water alone as a solvent or dispersing medium and at a temperature of 90° C. to 100° C.

2. In a process of producing a polymeric polyol in an aqueous reaction system in the presence of an alkali metal hydroxide catalyst, the improvement to produce a polymeric polyol of high molecular weight, low unsaturation, high functionality with reduced by-product production and extended polymeric chains in a reaction which comprises the steps of reaction only one kind of a polyhydroxy compound having at least three hydroxyl groups in its molecule and being selected from the group consisting of tetrols, pentols, hexols, and monosaccharide, disaccharide and trisaccharide sugars with ethylene oxide, propylene oxide or a mixture thereof in the presence of an alkali metal hydroxide catalyst used in an amount of 10% to 20% by mole based on the molar amount of the polyhydroxy compound, said reaction being carried out in the presence of a liquid medium essentially consisting of water alone as a solvent or dispersing medium and at a temperature of 90° C. to 100° C., and after distilling out water from the reaction mixture, reacting the resultant polymeric polyol reaction product with ethylene oxide, propylene oxide or a mixture thereof in the presence of an alkali metal hydroxide catalyst used in an amount of 10% to 80% by mole based on the molar amount of said polymeric polyol reaction product at a temperature of room temperature to 100° C.

3. A process as claimed in claim 1 wherein the improvement further comprising that the alkali metal hydroxide is potassium hydroxide.

4. A process as claimed in claim 1 wherein the improvement further comprising that the polyhydroxy compound is pentaerythritol.

5. A process as claimed in claim 1 wherein the improvement further comprising that the polyhydroxy compound is D-sorbitol.

6. A process as claimed in claim 1 wherein the improvement further comprising that the polyhydroxy compound is sucrose.

7. A process as claimed in claim 1 wherein the improvement further comprising that the reaction is conducted at a maximum temperature of 90°–95° C.

8. A process as claimed in claim 1 wherein the improvement further comprising that the reaction is conducted under pressure.

9. A process as claimed in claim 2 wherein the improvement further comprises that the resultant polymeric polyol reaction product is reacted under substantially anhydrous conditions.

10. A process as claimed in claim 2 wherein the improvement further comprises that the catalyst is finely divided.

11. A process as claimed in claim 2 wherein the improvement further comprises that the resultant polymeric polyol reaction product is reacted at a maximum temperature of 90°–95° C.

12. A process as claimed in claim 2 wherein the improvement further comprises that the resultant polymeric polyol reaction product is reacted under pressure.

* * * * *